United States Patent [19]
Gvaryahu et al.

[11] Patent Number: 4,913,092
[45] Date of Patent: Apr. 3, 1990

[54] METHOD OF RAISING PRECOCIAL BIRDS UTILIZING FILIAL IMPRINTING, ENVIRONMENTAL ENRICHMENT, AND MUSIC

[75] Inventors: Gadi Gvaryahu; Danis L. Cunningham, both of Ithaca, N.Y.

[73] Assignee: Cornell Research Foundation, Inc., Ithaca, N.Y.

[21] Appl. No.: 58,116

[22] Filed: Jun. 4, 1987

[51] Int. Cl.$^4$ ............................................. A01K 31/00
[52] U.S. Cl. ........................................ 119/1; 119/29
[58] Field of Search ........................ 119/1, 29, 45, 48

[56] References Cited

U.S. PATENT DOCUMENTS 4,313,397 2/1982 Markum ................................ 119/29

FOREIGN PATENT DOCUMENTS 78705 5/1986 Israel .

OTHER PUBLICATIONS

Gvaryahu, G. et al., Application of the Filial Imprinting Phenomenon on Commercial Farm Broiler Chicks (1987).
Christensen, A. C. et al., Observations on the Effects of Music Exposure to Growing Performance of Meat-Type Chicks; Poultry Science 54:619–621 (1975).
Jones, R. B. et al., Growth and the Plasma Concentrations of Growth Hormone and Prolactin in Chicks: Effects of "Environmental Enrichment", Sex and Strain; British Poultry Science 21:457–462 (1980).
Belanovskii A. S. et al., Acoustic Stress in Commercial Poultry Production (1982).
Cliften, P. G., The Synchronization of Feeding in Domestic Chicks by Sound Alone; Animal Behavior, 1979, 27, 829–832.
Shreck, P. K. et al., Environmental Factors in the Development of Eating in Chicks (1962).
Gaioni, S. S., et al., Effects of Group Rearing on the Control Exerted by an Imprinting Stimulus; Animal Learning and Behavior (1980).
Wood-Gush, D. G. M. et al., The Enrichment of a Bare Environment for Animals in Confined Conditions; Applied Animal Ethology 10 (1983) 209–217.
Jones, R. B., et al., Effects of Regular Handling on Growth in Male and Female Chicks of Broiler and Larger Strains; British Poultry Science 22:461–465 (1981).
Gross, W. B. et al., Socialization as a Factor in Resistance to Infection, Feed, Efficiency, and Response to Antigen in Chickens; Am. J. Vet. Res., vol. 43, No. 11, (1981).

Primary Examiner—Paul J. Hirsch
Attorney, Agent, or Firm—Jones, Tullar & Cooper

[57] ABSTRACT

A method for improving feeding habits, mortality rates, and overall behavior in precocial birds as they are raised combines the effects of filial imprinting, environmental enrichment, and music. One or more filial imprinting objects are disposed in a pen in which the birds, such as young heavy strain chicks, are raised. A sound system is includes with the objects to provide soothing music, such as classical music, intermittently. To further improve the living environment, a source of heat, such as an infrared bulb, is disposed in the pen, and soft texture material is placed on the imprinting objects. Significant improvements in feeding habits, mortality rates, and overall behavior are achieved with this method.

5 Claims, No Drawings

METHOD OF RAISING PRECOCIAL BIRDS UTILIZING FILIAL IMPRINTING, ENVIRONMENTAL ENRICHMENT, AND MUSIC

BACKGROUND OF THE INVENTION

The present invention relates to a method of combining filial imprinting, environmental enrichment, and musical sounds, to improve behavioral characteristics, feeding habits, and mortality rates, in domestic precocial birds as they are raised.

Filial imprinting, the attachment of young birds to the first object they encounter, is a widely studied phenomenon. The attachment of precocial birds to an imprinting object may be expressed as physical contact, approach response, orienting movements, or reduction of stress behavior. Experiments with 10 day old chicks have suggested that the use of an imprinting stimulus or commonal feeding may have an effect on weight gain in young chicks as compared to chicks fed in isolation. Recent experiments have shown that large populations of heavy strain chicks can be attached to an imprinting stimulus, and the imprinting objects can then be used to move birds from a training area to a new location. In addition to facilitating movement, imprinted chicks spatially distributed themselves more equally in a new area around the imprinting objects. In this initial study, the imprinting objects provided recorded bird sounds to enhance the imprintability of the chicks.

The present inventors have newly observed that imprinted chicks appeared to be less fearful than controls. In addition, imprinted chicks appeared to feed more frequently.

Environmental enrichment involves the increase of stimulus value of the home environment by increasing its complexity. There is considerable evidence that environmental enrichment results in marked behavioral and physiological effects on mammals. In contrast to the many mammalian studies, very little is known about the effect of environmental enrichment on birds. In one study, however, it was found that environmental enrichment improved body weight gain, relative body weight gain and gain:food ratio in 9 day old broiler chicks.

Music has been associated with the treatment of human disease since ancient times, and its many physiological and psychological effects on humans is well known. Effects of music on animals, however, has not been well studied. Popular publications report that music can be used to increase milk production in diary cows, and recent studies indicate that swine may also respond in a favorable manner. No significant influence of music on precocial birds has been previously demonstrated. In one study, meat type chicks were exposed to different kinds of continuous music, and it was stated that low level dinner music improved body gain weight and food:gain ratio very slightly, though the data was not statistically significant.

Until now, the use of filial imprinting, environmental enrichment, and music in combination to improve behavioral characteristics, feeding habits, and mortality rates in precocial birds has not been suggested or attempted. It has now been found experimentally, that this triple combination has a significant effect on these parameters.

SUMMARY OF THE INVENTION

It is therefore the object of the present invention to provide a method for raising precocial birds, wherein the behavioral characteristics, feeding habits, mortality rates, and overall health and quality of the birds are significantly improved, and the raising process is thereby made more efficient and economical.

This, and other objects of the invention, are achieved by exposing precocial birds, as they are raised, to the combined effects of filial imprinting, environmental enrichment, and musical sounds. In the preferred embodiment of the invention, red or blue colored objects are utilized as filial imprinting objects, and are placed in the living area of the birds. A sound system is also provided with the objects to generate music. Environmental enrichment is attained through the use of heat near the imprinting objects, and soft textured material on the objects, both of which appear to increase the tendency of chicks to remain near the imprinting object.

Using the above method, experiments have shown significant increases in the percentage of birds feeding and the body weight of the birds, and significant decreases in the amount of food consumed to body weight gained ratio, mortality rate, and fear.

DETAILED DESCRIPTION OF THE PREFERRED EMBODIMENT OF THE INVENTION

Turning now to a more detailed consideration of the invention, controlled experiments were conducted on flocks of heavy strain chicks. One flock of chicks was subjected to filial imprinting, environmental enrichment, and music, while a second flock of chicks was used as the control group, and not exposed to any of these stimuli.

The experimental group was disposed in a pen containing one or more imprinting or enrichment objects of predetermined shape or color. In the experiments, good results were obtained with one or more blue plastic cubes or boxes having sides of between about 10 cm and 50 cm in length. It has been established that chicks unlearned color preferences are bimodal, with peaks at short and long wavelengths. This explains the results of the experiments conducted in conjunction with the present invention, in which it was found that a large group of broiler chicks preferred to follow blue or red objects. Thus, the selected color of the imprinting object is important.

Chicks are also known to be attracted to heat and soft textured materials. Environmental enrichment was thus attained in the experiment by providing an infrared bulb, or other kind of heat radiator proximate and preferably above the imprinting object. The temperature apparent to the chicks from the radiation source should be above the ambient temperature but obviously below a temperature that causes discomfort and harm to the chicks. Also, a soft textured material was disposed on each box to provide soft contact between the chicks and the imprinting object. In the experiment, good results were obtained with red gloves hanging from the box at a chick's eye level although clearly, any soft textured material would probably suffice.

To provide music, a loudspeaker was located in each of the boxes that were activated simultaneously from a tape recorder. Good results were obtained with soft or soothing music, such as classical music. While the sound system can be activated continually, generally, the sound system was activated intermittently, for example for a period of between 30 minutes and 2 hours, alternating with an intermission of about the same duration.

The following table shows the results of the experiment, and presents values that are averages between all chicks, including males and females, in each group:

|  | % of Birds feeding | Body weight(g) | Food:Gain ratio | Mortality (%) | T.I. (sec) |
|---|---|---|---|---|---|
| control | 9.4 | 2573 | 2.00 | 5 | 165 |
| experimental | 13.6 | 2629 | 1.96 | 2.5 | 94 |

In the experiment, the percentage of birds feeding, body weight, and food:gain ratio measurements were taken on the chicks at 8 weeks of age. The mortality percentage was taken at the first two weeks, and duration of tonic immobility (T.I.), which is considered to be a fear potentiated response, was taken at 6-7 weeks of age.

As can be seen from the results, the chicks exposed to the imprinting and enrichment process and music spent significantly more time near the feeders than did the chicks in the control group. The percentage of birds feeding in the experimental group was approximately 45% greater than those feeding in the control group. As a result, body weight increased (about 2% on average, though 3% for males), and the food:gain ratio decreased (about 2%). Significantly, the mortality rate was 50% lower in the experimental group than it was in the control group. Also, in several kinds of fear tests, the experimental group was found to be significantly less fearful than the control group.

While the experimental measurements were as described, the time frame for practicing the invention is not unduely critical, for example the conjoint use of the several factors can be applied, for example from near with for at least about 2 weeks, preferably about 4 weeks more preferably 6 weeks and most preferably at least about 8 weeks.

This experiment provided for the first time, a management program for raising heavy strain chicks that incorporates filial imprinting, environmental enrichment, and music. Through combination of these three effects, surprising improvements in feeding habits, mortality rates, and overall behavior have been obtained.

Although the present invention has been disclosed in terms of a particular experimental arrangement, it will be apparent that numerous variations and modifications could be made to the arrangement without departing from the true spirit and scope of the invention, as set forth in the following claims. For example, the size, shape, color, material, and temperature of the imprinting object could all be varied, as well as the type and duration of the music played. The key to the invention is that all three of the effects; filial imprinting, environmental enrichment, and music, are combined to obtain the desired result.

We claim:

1. A method for raising young precocial birds comprising the steps of:
    disposing a flock of young precocial birds in a pen with at least one filial imprinting object;
    playing soft, soothing music to the flock of young precocial birds in the pen; and,
    enriching the environment of the flock of young precocial birds by disposing at least one soft textured object in the pen;
    whereby, the flock's feeding habits and general behavior are improved.

2. The method of claim 1, wherein the step of disposing comprises disposing a flock of young precocial birds in a pen with at least one blue or red cube that acts as a filial imprinting object.

3. The method of claim 1, further comprising the step of providing heat to the flock of young precocial birds to further enrich their environment.

4. The method of claim 1 wherein the step of playing soft, soothing music comprises playing classical music intermittently to the flock of young precocial birds in the pen.

5. A method for raising young precocial birds comprising the steps of:
    disposing a flock of young precocial birds in a pen with at least one blue or red cube that acts as a filial imprinting object;
    playing soft, soothing classical music intermittently to the flock in the pen; and,
    enriching the environment of the flock by disposing at least one soft textured object in the pen and providing heat to the flock with a heat radiator disposed proximate to the pen;
    whereby, the feeding habits and general behavior of the flock of young precocial birds are improved.

* * * * *